United States Patent [19]

Stolka et al.

[11] 4,052,205

[45] Oct. 4, 1977

[54] PHOTOCONDUCTIVE IMAGING MEMBER WITH SUBSTITUTED ANTHRACENE PLASTICIZER

[75] Inventors: Milan Stolka, Fairport; John F. Yanus, Webster, both of N.Y.

[73] Assignee: Xerox Corporation, Stamford, Conn.

[21] Appl. No.: 616,464

[22] Filed: Sept. 24, 1975

[51] Int. Cl.$^2$ ............... G03G 5/04; G03G 5/06; G03G 5/08

[52] U.S. Cl. .................... 96/1 PC; 96/1 R; 96/1.5 R; 260/671 P

[58] Field of Search ............ 96/1.5, 114.4; 252/501; 260/668 R, 668 F, 671 P

[56] References Cited

U.S. PATENT DOCUMENTS

| | | | |
|---|---|---|---|
| 3,549,361 | 12/1970 | Miller | 96/1.5 |
| 3,923,762 | 12/1975 | Stolka et al. | 96/1.5 |
| 3,928,034 | 12/1975 | Regensburger | 96/1.5 |
| 3,937,631 | 2/1976 | Eisenhut | 96/1.5 |

OTHER PUBLICATIONS

Chem. Abstr., vol. 70, 1969, 4925y –Plasticizing of Polymers Studied by Thermographic Methods.
Chem. Abstr., vol. 71, 113582a –Plasticization of Polymers Studied by Differential Thermal Analysis, (1969).

*Primary Examiner*—Roland E. Martin, Jr.
*Attorney, Agent, or Firm*—James J. Ralabate; James Paul O'Sullivan; Ronald L. Lyons

[57] ABSTRACT

Novel photoconductive imaging members are provided comprising a layer of inorganic photoconductive material contained on a supporting substrate with a contacting layer of an electrically active organic material contiguous with the photoconductive layer comprising a plasticizer of an alkyl substituted anthracene.

14 Claims, 4 Drawing Figures

PHOTOCONDUCTIVE IMAGING MEMBER WITH SUBSTITUTED ANTHRACENE PLASTICIZER

BACKGROUND OF THE INVENTION

Photoconductive imaging members comprising a layer of inorganic photoconductive material such as amorphous selenium contained on a supporting substrate and a contacting layer of an electrically active organic material contiguous with the photoconductive layer such as poly(N-vinyl carbazole) (PVK) are known. Many of the inorganic photoconductive materials are excellent for generating charges while particular organic materials such as PVK, poly(vinyl anthracene), poly (vinylpyrene) and the like, are excellent for transporting charges but are brittle so that difficulties have been encountered in fabricating, e.g. in melt extrusion, heat pressing, etc. Moreover, the mechanical properties of these high molecular weight polymers are often poor so that they tend to craze. It has been found that the glass transition temperature may be decreased and crazing eliminated so as to increase the ductility of the polymer by the addition of plasticizers. However, the addition of compounds commonly used as plasticizers has been found to cause charge trapping or other adverse interference with the electrical properties of the polymer. Thus, the provision of plasticizers would be desirable which would not interfere with the electrical properties but would contribute to the transport of electric charges of the polymer and also eliminate crazing and increase its ductility.

BRIEF SUMMARY OF THE INVENTION

It has now been discovered that improved photoconductive imaging members can be provided comprising a layer of a photoconductive material generally contained on a supporting substrate with a contiguous layer of an electrically active organic material when the electrically active organic material comprises a polymer capable of receiving and transporting charges plasticized with an alkyl substituted anthracene of the formula:

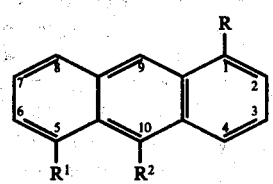

wherein R and $R^1$ are alkyl groups of from 3 to 12 carbons, preferably branched, or one of said groups is a hydrogen atom, $R^2$ is the same as R and $R^1$ or a chloro or bromo atom and wherein at least one of said groups is an alkyl. Surprisingly, it has been found that the alkyl substituted anthracenes described above decrease the glass transition temperature of brittle polymers such as PVK so as to improve the mechanical properties and render them ductile so as to reduce crazing upon flexure, without interfering with the desirable electrical properties of the polymer. In addition, the aforesaid alkyl substituted anthracenes have unusually high solubility in various polymers so as to form molecular dispersions with no apparent sign of crystallinity up to very high loadings of well over 50 percent even after the imaging member is stored for considerable periods up to six months or more, but is effective at amounts as slow as 1%. A preferred range both for results and economy of operation is between about 4 and about 10 percent. In addition, said alkyl substituted anthracenes contribute beneficially to the imaging member because they transport holes injected into the transport matrix by either inorganic or organic photoconductive materials. In addition, the alkyl substituted anthracenes are easy to synthesize and do not form charge transfer complexes with the active polymers such as PVK.

DETAILED DESCRIPTION OF THE INVENTION

Figure 1:
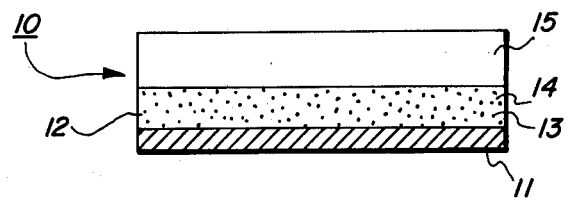
FIG. 1 is a schematic illustration of one embodiment of a device of the invention.

The imaging member of the invention comprises at least two operative layers. The first layer comprises a layer of photoconductive material which is capable of photogenerating and injecting photo-excited holes into a contiguous or adjacent active material. The active material comprises a transparent organic polymer or nonpolymeric insulating material which is substantially non-absorbing to visible light or radiation in the region of intended use, but which is active in that it allows the injection of photo-excited holes from the photoconductive layer and allows these holes to be transported through the active layer to selectively discharge a surface charge on the free surface of the active layer.

It should be understood that the active layer does not function as a photoconductor in the wavelength region of use. Hole-electron pairs are photogenerated in the photoconductive layer and the holes are then injected into the active layer and hole transport occurs through the active layer.

A typical application of the instant invention includes the use of a sandwich cell or layered configuration which in one embodiment consists of a supporting substrate such as a conductor containing a photoconductive layer thereon. For example, the photoconductive layer may be in the form of a layer of amorphous, trigonal or vitreous selenium. A transparent polymeric layer comprising an electrically active material containing an alkyl substituted anthracene dispersed therein which allows for hole injection and transport, is coated over the selenium photoconductive layer. Generally, a thin interfacial barrier or blocking layer is sandwiched between the photoconductive layer and the active layer. This barrier layer may comprise any suitable electrically insulating material such as metallic oxide or organic resin. The use of the transparent active polymer layer allows one to take advantage of placing a photoconductive layer adjacent to a supporting substrate, and protecting the photoconductive layer with a top surface which will allow for the transport of photo-excited holes from the photoconductor, and at the same time function to physically protect the photoconductive layer from environmental conditions. The position of the photoconductive and active material layers, however, can be reversed. This structure can then be imaged in the conventional xerographic manner which usually includes charging, optical projection exposure and development.

If desired, an electrically insulating substrate may be used. In this instance, the charge may be placed upon the imaging member by double corona charging techniques well known and disclosed in the art. Other modifications using an insulating substrate or no substrate at all include placing the imaging member on a conductive backing member or plate and charging the surface while in contact with said backing member. Subsequent to imaging, the imaging member may then be stripped from the conductive backing.

As defined herein, a photoconductor is a material which is electrically photoresponsive to light in the wavelength region in which it is to be used. More specifically, it is a material whose electrical conductivity increases significantly in response to the absorption of electromagnetic radiation in a wavelength region in which it is to be used. This definition is necessitated by the fact that a vast number of aromatic organic compounds are known or expected to be photoconductive when irradiated with strongly absorbed ultraviolet, X-ray, or gamma-radiation. Photoconductivity in organic materials is a common phonemenon. Practically all highly conjugated organic compounds exhibit some degree of photoconductivity under appropriate conditions. Many of these organic materials have their prime wavelength response in the ultraviolet. However, little commercial utility has been found for ultraviolet responsive materials, and their short wavelength response is not particularly suitable for document copying or color reproduction. In view of the general prevalence of photoconductivity in organic compounds following short wavelength excitation, it is therefore necessary that for the instant invention, the term "photoconductor" or "photoconductive" be understood to include only those materials which are in fact photoresponsive in the wavelength region in which they are to be used.

The active material or transport material, which is also referred to as the active matrix material, is a substantially non-photoconductive material in the visible light spectrum and which receives and transports photo-excited holes from the photoconductive layer at an efficiency of at least about 10 percent at fields of about $2 \times 10^5$ volts/cm. This material is further characterized by the ability to transport the carrier at least $10^{-3}$ cm. at a field of no more than about $10^6$ volts/cm. In addition, the active material is substantially transparent in the wavelength region in which the device is to be used.

The active transport material which is employed in conjunction with the photoconductive layer in the instant invention is a material which is an insulator to the extent that an electrostatic charge placed on said active binder material is not conducted in the absence of illumination, at a rate sufficient to prevent the formation and retention of an electrostatic latent image thereon. In general, this means that the specific resistivity of the active transport material should be at least about $10^{10}$ ohm-cms.

As can be seen from the above discussion, most materials which are useful for active layers of the instant invention are incidentially also photoconductive when radiation of wavelengths suitable for electronic excitation is absorbed by them. However, photoresponse in the short wavelength region, which falls outside the spectral region for which the photoconductor is to be used, is irrelevant to the performance of the device. It is well known that radiation must be absorbed in order to generate photoconductive response, and the transparency criteria stated above for the active materials implies that these materials do not contribute significantly to the photoresponse of the photoreceptor in the wavelength region of use.

The reason for the requirement that the active material should be transparent is so that most of the incident radiation is utilized by the charge carrier generator layer for efficient photo-injection. An advantage of the layered photosensitive member of the invention is that it can be charged to a higher surface potential at comparable thicknesses than the systems known in the prior art.

It is not the intent of this invention to restrict the choice of active materials to those which are transparent in the entire visible region. For example, when used with a transparent substrate, imagewise exposure may be accomplished through the substrate without the light passing through the layer of active material. In this case the active material need not be non-absorbing in the wavelength of use. Other applications where complete transparency is not required for the active material in the visible region include the selective recording of narrow-band radiation such as that emitted from lasers, spectral pattern recognition and possible functional color xerography such as color coded form duplication.

Referring to FIG. 1 reference character 10 designates an imaging member in the form of a plate which comprises a supporting substrate 11 having a binder layer 12 thereon, and an active layer 15 positioned over binder layer 12. Substrate 11 is preferably made up of any suitable conductive material. Typical conductors comprise aluminum, steel, brass or the like. The substrate may be rigid or flexible and of any convenient thickness. Typical substrates include flexible belts or sleeves, sheets, webs, plates, cylinders, and drums. The substrate or support may also comprise a composite structure such as a thin conductive coating contained on a paper base; a plastic coated with a thin conductive layer such as aluminum or copper iodide; or glass coated with a thin conductive coating of chromium or tin oxide.

Binder layer 12 contains photoconductive particles 13 dispersed randomly without orientation in a binder 14. The photoconductive particles may consist of any suitable inorganic or organic photoconductor and mixtues thereof. Inorganic materials include inorganic crystalline compounds and inorganic photoconductive glasses. Typical inorganic crystalline compounds include cadmium sulfoselenide, cadmium selenide, cadmium sulfide, and mixtures thereof. Typical inorganic photoconductive glasses include amorphous selenium, and selenium alloys such as selenium-tellurium, and selenium-arsenic. Selenium may also be used in a crystalline form known as trigonal selenium. Typical organic photoconductive materials include phthalocyanine pigments such as the X-form of metal free phthalocyanine described in U.S. Pat. No. 3,357,989 to Byrne et al, metal phthalocyanines, such as copper phthalocyanine; quinacridones available from DuPont under the Tradename Monastral Red, Monastral Violet, and Monastral Red Y; substituted 2,4-diamino-triazines disclosed by Weinberger in U.S. Pat. No. 3,445,227; triphenodioxazines disclosed by Weinberger in U.S. Pat. No. 3,442,781; polynuclear aromatic quinones available from Allied Chemical Corp. under the Tradename Indofast Double Scarlet, Indofast Violet Lake B, Indofast Brilliant Scarlet, and Indofast Orange.

Inter-molecular charge transfer complexes, such as a mixture of poly-N-vinyl carbazole (PVK) and trinitrofluorenone (TNF) may be used as charge generator material. These materials are capable of injecting photo-excited holes into the transport material.

Additionally, intra-molecular charge transfer complexes, such as those disclosed in Limburg et al, U.S. Pat. No. applications Ser. No. 454,484, filed Mar. 25, 1974; Ser. No. 454,485, filed Mar. 25, 1974; Ser. No. 454,486, filed Mar. 25, 1974; Ser. No. 454,487, filed Mar. 25, 1974; Ser. No. 374,157, filed June 27, 1973, now abandoned; and Ser. No. 374,187, filed June 27, 1973, now abandoned; may be used as charge generation material capable of injecting photo-excited holes into the transport material.

The above list of photoconductors should in no way be taken as limiting, but is merely illustrative of suitable materials. The size of the photoconductive particles is not particularly critical, but particles in a size range of about 0.01 to 1.0 microns yield particularly satisfactory results.

The binder material 14 may comprise any electrically insulating resin such as those disclosed in Middleton et al, U.S. Pat. No. 3,121,006, or any suitable active material which may be the same or different from that used for layer 15. When using an electrically inactive or insulating resin it is essential that there be particle-to-particle contact between the photoconductive particles. This necessitates that the photoconductive material be present in an amount of at least about 25 percent by volume of the binder layer with no limitation on the maximum amount of photoconductor in the binder layer. If the matrix or binder comprises an active material, the photoconductive material need only comprise about 1 percent or less by volume of the binder layer with no limitation on the maximum amount of photoconductor in the binder layer. The thickness of the photoconductive layer is not critical. Layer thicknesses from about 0.05 to 20 microns have been found satisfactory, with a preferred thickness of about 0.2 to 5 microns yielding good results.

Active layer 15 may comprise any suitable transparent organic polymer or nonpolymeric material capable of supporting the injection of photo-excited holes from the photoconductive layer and allowing the transport of these holes through the organic layer to selectively discharge a surface charge. Polymers having this characteristic have been found to contain repeating units of a polynuclear aromatic hydrocarbon which may also contain heteroatoms such as, for example, nitrogen, oxygen, or sulfur. Typical active polymers include poly-N-vinyl carbazole (PVK), poly-1-vinyl pyrene (PVP), poly-9-vinyl anthracene, poly [1-(2-anthryl)-ethyl methacrylate], polyacenaphthalene, poly-9-(4-pentenyl)-carbazole, poly-9-(5-hexyl)-carbazole, poly-methylene pyrene, poly-1-(-αpyrenyl)-butadiene and N-substituted polymeric acrylic acid amides of pyrene. Also included are derivatives of such polymers including alkyl, nitro, amino, halogen, and hydroxy substituted polymers. Typical examples are poly-3-amino carbazole, poly (N-vinyl-1,3-dibromocarbazole) and poly(N-vinyl-3,6-dibromocarbazole) and particular derivatives of the formula

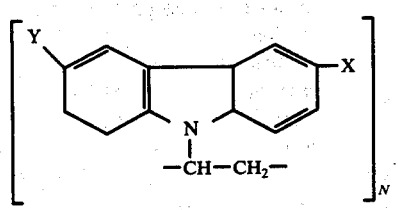

where X and Y are substituents and N is an integer. Also included are structural isomers of these polymers, typical examples include poly-N-vinyl carbazole, poly-2-vinyl carbazole and poly-3-vinyl carbazole. Also included are copolymers; typical examples are N-vinyl carbazole/methyl acrylate copolymer and 1-vinyl pyrene/butadiene ABA, and AB block polymers. Typical nonpolymeric materials include carbazole, N-ethylcarbazole, N-phenylcarbazole, pyrene, tetraphene, 1-acetylpyrene, 2,3-benzochrysene, 6,7-benzopyrene, 1-bromopyrene, 1-ethylpyrene, 1-methylpyrene, perylene, 2-phenylindole, tetracene, picene, 1,3,6,8-tetraphenylpyrene, chyrsene, fluorene, fluorenone, phenanthrene, tripheylene, 1,2,5,6-dibenzanthracene, 1,2,3,4-dibenzanthracene, 2,3-benzopyrene, anthranquinone, dibenzothiophene, and naphthalene and 1-phenylnaphthalene. Due to the poor mechanical properties of the nonpolymer materials they are preferably used in conjunction with either an active polymeric material or a non-active polymeric binder. Typical examples include suitable mixtures of carbazole in poly-N-vinyl carbazole as an active polymer and carbazole in a non-active binder. Such non-active binder materials include polycarbonates, acrylate polymers, polyamides, polyesters, polyurethanes, and cellulose polymers.

It should be understood that the use of any active polymer whose repeat unit contains the appropriate aromatic hydrocarbon, such as carbazole, and which supports hole injection and transport, may be used. It is not the intent of the invention to restrict the type of polymer which can be employed as the transport layer. Polyesters, polysiloxanes, polyamides, polyurethanes and epoxies as well as block, random or graft copolymers (containing the aromatic repeat unit) are exemlary of the various types of polymers which can be employed as the binder for active material. In addition suitable mixtures of active polymers with inactive polymers or non-polymeric materials may be employed. One action of certain non-active material is to act as a plasticizer to improve the mechanical properties of the active polymer layer. Typical plasticizers include epoxy resins, polyester resins, polycarbonate resins, 1-phenyl naphthalene and chlorinated diphenyl.

The active layer not only serves to transport holes, but also protects the photoconductive layer from abrasive or chemical attack and therefore extends the operating life of the photoreceptor imaging member.

In general, the thickness of the active layer should be from about 5 to 100 microns, but thicknesses outside this range can also be used. The ratio of the thickness of the active layer to the photoconductor layer should be maintained from about 2:1 to 200:1, and in some instances as great as 400:1.

In another embodiment of the instant invention, the structure of FIG. 1 is modified to insure that the photoconductive particles are in the form of continuous chains through the thickness of binder layer 12. This embodiment is illustrated in FIG. 2 in which the basic structure and materials are the same as those of FIG. 1, except that the photoconductive particles 13 are in the form of continuous chains.

Alternately, the photoconductive layer may consist entirely of a substantially homogeneous unoriented photoconductive material such as a layer of amorphous selenium, a selenium alloy, or a powdered or sintered photoconductive layer such as cadmium sulfoselenide or phthalocyanine. This modification is illustrated by FIG. 3 in which a photosensitive member 30 comprises a substrate 11, having a homogenous photoconductive layer 16, with an overlaying active organic layer 15.

Figure 2:
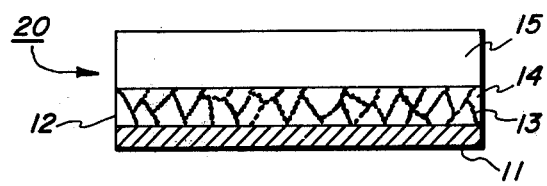
FIG. 2 illustrates a second embodiment of a device for the invention.
Figure 3:
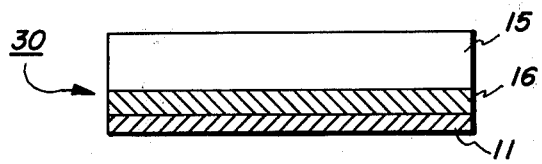
FIG. 3 illustrates a third embodiment of a device for the invention.
Figure 4:
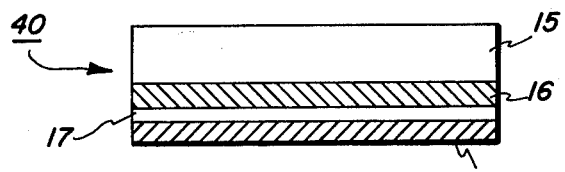
FIG. 4 illustrates a fourth embodiment of a device of the invention.

Another modification of the layered configurations described in FIGS. 1, 2 and 3 includes the use of a blocking layer 17 at the substrate-photoconductor interface. This configuration is illustrated by photosensitive member 40 in FIG. 4 in which the substrate 11, and photoconductive layer 16 are separated by a blocking layer 17. The blocking layer functions to prevent the injection of charge carriers from the substrate into the photoconductive layer. Any suitable blocking material may be used. Typical materials include nylon, epoxy, and aluminum oxide.

As stated above, the photoconductor material, whether it be in the form of a pigment or as a homogeneous layer, is preferably employed in an unoriented manner. By unoriented, it is meant that the pigment or photoconductive layer is isotropic with respect to the exciting electromagnetic radiation, i.e., it is equally sensitive to any polarization of the exciting radiation.

In general, the structure of the device of the instant invention requires that the photoconductor and active organic material be selected or matched to provide for the active layer to be non-absorbing to light in the wavelength region used to generate photo-excited carriers in the photoconductive layer. This preferred range for xerographic utility is from about 4000–8000 Angstrom Units. In addition, the photoconductor should be responsive to all wavelengths from 4000 to 8000 Angstrom Units if panchromatic response is required. All photoconductor-active material combinations of the instant invention result in the injection and subsequent transport of holes across the physical interface between the photoconductor and active material.

Although the active material may comprise any suitable polymer or non-polymeric material having the required properties, polymeric materials are preferred in that their physical properties, such as flexibility, are generally superior to the physical properties of the non-polymeric materials.

The following examples will serve to illustrate the invention. All parts and percentages in said examples and elsewhere in the specification and claims are by weight unless specified.

EXAMPLE I

Preparation of 1-Acetyl Anthracene

Into a 5 liter round bottomed flask fitted with a mechanical stirrer and dropping funnel is placed 90 grams (0.5 mole) of anthracene. The flask is flushed with argon to remove air and approximately 1.5 liters of methylene chloride added to the flask through the funnel. The flask is then placed in ice. To a second 3 liter flask placed in ice is added 900 milliliters of methylene chloride followed by 130 grams (1.0 mole) of aluminum chloride with constant and vigorous agitation. Acetyl chloride (43 ml., 0.6 mole) is added dropwise and the mixture allowed to stir over ice for 5 to 10 minutes.

To the first flask containing the anthracene/methylene chloride mixture is added a small amount of aluminum chloride (about 2.5 grams) to insure an excess of aluminum chloride from the start of the reaction. The aluminum chloride/methylene chloride complex of the second flask was then added to the first flask through the funnel over a period of 20 to 30 minutes with constant and vigorous agitation. After two hours at 0.20 C under argon, a red solid material was filtered out, washed with methylene chloride and a small amount of hexane. It was then hydrolyzed by addition to a flask containing ice water and hydrochloric acid whereupon the color changed from red to greenish-yellow. The solid was filtered, washed with water and dried. The solid material which was a mixture of diacetyl anthraceneand 1-acetylanthracene was dissolved in refluxing benzene and allowed to cool to room temperature. Then the crystallized 1,5-diacetylanthracene was removed by filtering. The benzene was then evaporated from the liquid portion and the crude product was recrystallized from ethyl alcohol. The yield was 33 grams of 1-acetylanthracene. A repeated recrystallization gave a pure product of 1-acetylanthracene with a melting point of 106° C.

EXAMPLE II

Preparation of 1-(2-propyenyl) anthracene

Into a three-necked 1000 milliliter flask was added 64 grams of triphenylmethylphosphonium bromide (0.18 mole) and 300 milliliters of tetrahydrofuran over a nitrogen blanket. To this mixture was slowly added 85 milliliters of 2N Buli in hexane. The resultant orange-red colored solution was allowed to sit for 1 hour and a solution of 33 grams of 1-acetyl lanthracene (0.15 mole) in 125 milliliters of tetrahydrofuran, added dropwise. After the addition was complete, the heterogeneous mixture having a brown-yellow color was refluxed until dark brown for 5 hours. The mixture was refluxed for an additional 15 hours, extracted with hexane and then a mixture of hexane and benzene (4:1) to yield 28 grams of light yellow oil having a melting point of 23.5°–24° C which was identified as 1(2 propenyl) anthracene.

EXAMPLE III

Preparation of 1-isopropyl anthracene

Into a 500 milliliter hydrogenation bottle was placed 0.2 grams of 5% palladium on carbon, 10 grams of 1-(2-propenyl) anthracene and 200 milliliters of hexane and the bottle flushed three times with hydrogen. Hydrogen was fed into the bottle at an initial pressure of 23 pounds per square inch which after 3 days had a final pressure of 19 pounds per square inch. The mixture was filtered, evaporated to an oil and chromatographed on basic alumina with hexane. The mixture was washed with a 10:1 mixture of hexane and benzene and distilled to recover a fraction of pure isopropyl anthracene having a melting point of 36°–36.5° C.

EXAMPLE IV

A series of plates were prepared in which amorphous selenium was vapor deposited to a thickness of 0.5 u on a substrate of aluminum, and a poly(N-vinyl carbazole) (PVK) plasticized with from 1 to 35 mole percent 1-isopropyl anthracene coated onto the selenium layer to a thickness of 18 microns using a Gardner Laboratory Bird applicator. From the following data in which a non-plasticized PVK plate was used as a control, it can be seen that the 1-isopropyl anthracene was found to depress the glass transition temperature of PVK from 220° C to about 70° C with a loading of 35.0 mole percent of 1-isopropyl anthracene. It was also found that amounts in excess of about 4 percent 1-isopropyl anthracene eliminated crazing of the PVK. In addition, the plasticizer was found not to reduce the transfer of holes nor did it crystallize upon storage of the plate for extended periods up to six months.

|  | Tg, ° C |
|---|---|
| PVK | 220° C |
| PVK + 1.0 mole % 1-IPA | 210° C |
| PVK + 3.0 mole % 1-IPA | 187° C |
| PVK + 5.0 mole % 1-IPA | 182° C |
| PVK + 15.0 mole % 1-IPA | 105° C |
| PVK + 35.0 mole % 1-IPA | ~70° C |

EXAMPLE V

In accordance with the general procedures of Examples III and IV, 1,5-diisopropyl anthracene, 2-butyl isoamyl anthracene, 2-hexyl anthracene, 1,5-dimethyl anthracene, 1-ethyl, 10-chloro anthracene and 1,5-diethyl, 10-bromo anthracene are prepared and tested with a variety of brittle polymers including poly(vinyl anthracenes), PVK and poly(1-vinylpyrene), and similar results are obtained.

Having described the present invention with reference to these specific embodiments, it is to be understood that numerous variations can be made without departing from the spirit of the invention and it is intended to encompass such reasonable variations or equivalents within its scope.

What is claimed is:

1. An imaging member consisting essentially of a layer of photoconductive material and a contiguous layer of an electrically active organic material with the ratio of the thickness of the active layer to the photoconductive layer being maintained from about 2:1 to 200:1, said photoconductive layer exhibiting the capability of photo-excited hole generation and injection, said active organic material being capable of receiving and transporting the photo-excited holes from said photoconductive layer, wherein said active layer consists essentially of poly(N-vinylcarbazole) containing a plasticizing amount of a plasticizer selected from the group consisting of 1-isopropyl anthracene and 1,5-diisopropyl anthracene.

2. The member of claim 1 in which the photoconductive layer comprises photoconductive particles dispersed in a binder.

3. The member of claim 1 wherein the photoconductive layer overlies a substrate.

4. The member of claim 3 wherein the substrate is electrically conductive.

5. The member of claim 3 in which the photoconductive layer is contained on a substantially transparent supporting substrate.

6. The member of claim 1 in which the photoconductive layer comprises at least one material selected from the group consisting of vitreous selenium, a selenium alloy, trigonal selenium, cadmium sulfoselenide, and a mixture of poly-N-vinyl carbazole and trinitrofluorenone.

7. The imaging member of claim 1 wherein the photoconductive material comprises amorphous selenium.

8. The member of claim 1 wherein the photoconductive layer comprises a substantially homogeneous photoconductive material.

9. A method of imaging which comprises:
a. providing an imaging member consisting essentially of a layer of photoconductive material and a contiguous layer of an electrically active organic material with the ratio of the thickness of the active layer to the photoconductive layer being maintained from about 2:1 to 200:1, said photoconductive layer exhibiting the capability of photo-excited hole generation and injection, said active organic material being capable of receiving and transporting the photo-excited holes from said photoconductive layer, wherein said active layer consists essentially of poly(N-vinylcarbazole) containing a plasticizing amount of a plasticizer selected from the group consisting of 1-isopropyl anthracene and 1,5-diisopropyl anthracene;
b. then uniformly negatively electrostatically charging the free surface of the active layer; and
c. exposing said charged layer to a source of activating radiation to which the photoconductive layer is absorbing and to which the active layer is substantially transparent and non-absorbing, the exposure being in the form of a pattern of light and shadow optically projected toward said layer, whereby photo-excited holes generated by said photoconductive layer are injected into and transported through said active layer to form a latent electrostatic image on the free surface of the active layer.

10. The method of claim 9 in which the latent image is developed to form a visible image.

11. The method of claim 9 which the activating radiation is within the visible spectrum.

12. The method of claim 9 in which the source of activating radiation is in the range of about 4000 to 8000 Angstrom Units.

13. The method of claim 9 in which the substrate is electrically conductive.

14. A method of imaging which comprises:
a. providing an imaging member consisting essentially of a layer of photoconductive material and a contiguous layer of an electrically active organic material with the ratio of the thickness of the active layer to the photoconductive layer being maintained from about 2:1 to 200:1, said photoconductive layer exhibiting the capability of photo-excited hole generation and injection, said active organic material being capable of receiving and transporting the photo-excited holes from said photoconductive layer, wherein said active layer consists essentially of poly(N-vinylcarbazole) containing a plasticizing amount of a plasticizer selected from the group consisting of 1-isopropyl anthracene and 1,5-diisopropyl anthracene;
b. then uniformly negatively electrostatically charging the free surface of the active layer;
c. exposing said charged layer to a source of activating radiation to which the photoconductive layer is absorbing and to which the active layer is substantially transparent and non-absorbing the exposure being in the form of a pattern of light and shadow optically projected toward said layer, whereby photo-excited holes generated by said photoconductive layer are injected into and transported through said active layer to form a latent electrostatic image on the free surface of the active layer;
d. developing the latent image to form a visible image;
e. transferring the visible image to a receiving sheet, and
f. repeating steps (b), (c) and (d) at least one additional time.

* * * * *